(12) United States Patent
Patterson et al.

(10) Patent No.: US 8,864,685 B2
(45) Date of Patent: Oct. 21, 2014

(54) WIRE GUIDE HAVING TWO SAFETY WIRES

(75) Inventors: Donald Patterson, Bloomington, IN (US); Tamera Dees, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 439 days.

(21) Appl. No.: 13/246,311

(22) Filed: Sep. 27, 2011

(65) Prior Publication Data

US 2012/0101408 A1  Apr. 26, 2012

Related U.S. Application Data

(60) Provisional application No. 61/405,768, filed on Oct. 22, 2010.

(51) Int. Cl.
*A61B 5/00* (2006.01)
*A61M 25/09* (2006.01)

(52) U.S. Cl.
CPC ......... *A61M 25/09* (2013.01); *A61M 25/09033* (2013.01); *A61M 2025/091* (2013.01); *A61M 2025/09083* (2013.01)
USPC ...................................... 600/585

(58) Field of Classification Search
USPC ...................................... 600/585
See application file for complete search history.

(56) References Cited

U.S. PATENT DOCUMENTS

| | | | |
|---|---|---|---|
| 4,748,986 A * | 6/1988 | Morrison et al. | 600/585 |
| 4,763,647 A | 8/1988 | Gambale | |
| 4,779,628 A * | 10/1988 | Machek | 600/585 |
| 4,830,023 A | 5/1989 | de Toledo et al. | |
| 4,867,173 A | 9/1989 | Leoni | |
| 4,895,168 A | 1/1990 | Machek | |
| 4,934,380 A | 6/1990 | de Toledo | |
| 5,040,543 A | 8/1991 | Badera et al. | |
| 5,299,580 A | 4/1994 | Atkinson et al. | |
| 5,746,701 A | 5/1998 | Noone | |
| 6,245,030 B1 * | 6/2001 | DuBois et al. | 600/585 |
| 6,544,197 B2 | 4/2003 | DeMello | |
| 7,252,643 B2 * | 8/2007 | Fujimoto et al. | 600/585 |
| 2004/0039304 A1 * | 2/2004 | Connors et al. | 600/585 |
| 2005/0148901 A1 * | 7/2005 | Parins et al. | 600/585 |

* cited by examiner

*Primary Examiner* — Max Hindenburg
*Assistant Examiner* — Renee Danega
(74) *Attorney, Agent, or Firm* — Liell & McNeil

(57) ABSTRACT

A wire guide includes a helically wound coil having a proximal end and a distal end. A mandrel is positioned within the helically wound coil and terminates before the distal end of the helically wound coil. First and second safety wires are positioned within the helically wound coil and have proximal ends attached to the mandrel and distal ends attached to the distal end of the helically wound coil. The first and second safety wires are positioned on opposite sides of a distal tip of the mandrel and have contact surfaces facing the distal tip of the mandrel that have a shape other than convex. The interaction between the mandrel tip and the safety wires during a percutaneous vascular procedure inhibit mandrel protrusion and the potential tissue damage associated therewith.

6 Claims, 2 Drawing Sheets

WIRE GUIDE HAVING TWO SAFETY WIRES

RELATION TO OTHER PATENT APPLICATION

This application claims priority to provisional patent application 61/405,768, filed Oct. 22, 2010 with the same title.

TECHNICAL FIELD

The present disclosure relates generally to the field of vascular intervention, and more particularly to a wire guide having two safety wires for reducing mandrel protrusion during percutaneous endovascular procedures.

BACKGROUND

Diagnosis and treatment of vascular conditions are commonly performed using percutaneous endovascular procedures, which involve the insertion of a catheter or the like into a blood vessel or artery of the vascular system. Known catheterization procedures include the positioning and use of stents and balloons within constricted vessels or arteries, and the intravenous administration of bloods, drugs, and other fluids. The first step in the performance of these procedures is the establishment of a site through the skin by which access is made to the blood vessel or artery. A wire guide is then introduced into the vessel or artery and advanced to a desired location, often with the assistance of a guide catheter. A working catheter may then be advanced to the desired location over the wire guide in a safe and atraumatic fashion.

Wire guides typically include an elongate helically wound coil having a mandrel positioned therein for increasing the stiffness of the helically wound coil. The mandrel typically does not extend fully to a distal end of the helically wound coil, to allow increased flexibility at the distal end of the coil. This allows increased maneuverability through convoluted or tortuous pathways within the vascular system. Further, distal ends of the wire guides may be provided with preformed curves to further increase maneuverability of the wire guide into branches of vessels or arteries. Wire guides may also be provided with a single safety wire extending a length of the helically wound coil to reduce the possibility of portions of the helically wound coil breaking lose within a patient, should the helically wound coil unravel.

It is important for patient safety that a distal tip of the mandrel does not protrude through the helically wound coil while the wire guide is advanced through blood vessels or arteries of the patient. Such mandrel protrusion, which may scrape or puncture the inside of the vessel or artery through which the wire guide is moving, may become more likely when the flexible distal end of the helically wound coil is manipulated through sharp or tortuous curves of the vascular system.

The present disclosure is directed toward one or more of the problems set forth above.

SUMMARY OF THE DISCLOSURE

In one aspect, a wire guide includes a helically wound coil having a proximal end and a distal end. A mandrel is positioned within the helically wound coil and terminates before the distal end of the helically wound coil. First and second safety wires are positioned within the helically wound coil and have proximal ends attached to the mandrel and distal ends attached to the distal end of the helically wound coil. The first and second safety wires are positioned on opposite sides of a distal tip of the mandrel and have contact surfaces facing the distal tip of the mandrel that have a shape other than convex.

In another aspect, a method of making a wire guide includes attaching proximal ends of first and second safety wires to opposite sides of a mandrel such that substantially flat contact surfaces or substantially concave contact surfaces of the first and second safety wires face a distal tip of the mandrel. The method also includes inserting the mandrel and the first and second safety wires into a helically wound coil through a proximal end of the helically wound coil such that the mandrel terminates before a distal end of the helically wound coil. The method also includes welding distal ends of the first and second safety wires to the distal end of the helically wound coil.

DETAILED DESCRIPTION

Figure 1:
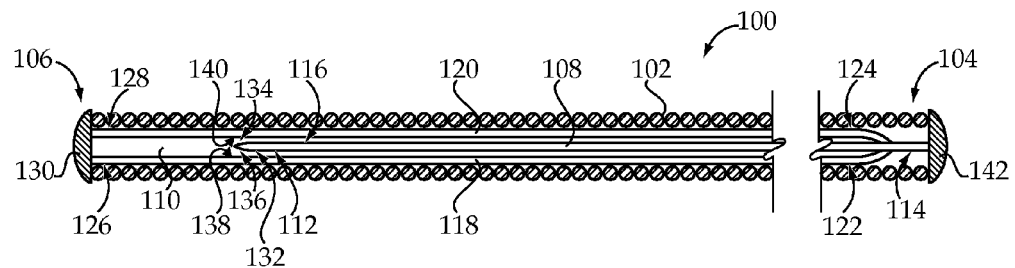
FIG. 1 is a sectional view of a wire guide according to one embodiment of the present disclosure.

Referring to FIG. 1, there is shown a first embodiment of a wire guide 100 that may be used in a variety of percutaneous endovascular procedures. The wire guide 100 generally includes a helically wound coil 102 having a proximal end 104 and a distal end 106. The helically would coil 102 may be made from stainless steel wire, or other similar material, and may be wound from a material having a round or other cross sectional shape. The helically wound coil 102 may be provided in any desired length and may have any outer diameter, suitable for the intended use of the wire guide 100. The helically wound coil 102 may preferably be coated with a lubricious polymer, such as Teflon, to facilitate smooth movement of the wire guide 100 within a catheter, with which the wire guide 100 is to be used, or a vascular structure of a patient. An inner diameter of the helically wound coil 102 may necessarily be of a size sufficient to house the components described herein.

A mandrel 108 is positioned within the helically wound coil 102 and, as shown, terminates before the distal end 106 of the helically would coil 102. Specifically, the mandrel 108 is received within a lumen, or cavity, 110 of the helically wound coil 102 and may extend a majority of a length of the coil 102. The mandrel 108 may be formed from stainless steel, or other commonly selected material, to provide increased stiffness of a majority of the wire guide 100, and may include a distal segment 112 that is tapered. The taper may be gradual or abrupt, and may begin at any position along the mandrel 108 from a proximal end 114 of the mandrel 108 to a distal end 116 of the mandrel 108.

First and second safety wires 118 and 120 are positioned within the helically wound coil 102 of wire guide 100. As shown, first and second safety wires 118 and 120 include proximal ends 122 and 124, respectively, attached to the mandrel 108, and distal ends 126 and 128, respectively, attached to the distal end 106 of the helically wound coil 102. Although the embodiment of FIG. 1 shows the proximal ends 122 and 124 of the safety wires 118 and 120 attached to the proximal end 114 of the mandrel 108, it should be appreciated that the proximal ends 122 and 124 may be attached at any position along the length of the mandrel 108. The distal ends 126 and 128 of the first and second safety wires 118 and 120 and the distal end 106 of the helically wound coil 102 are preferably joined together at a first weldment 130. The first weldment 130 may be formed using plasma welding or any other well known welding technique. Although welding or soldering may be preferred, it should be appreciated that other means for providing a strong and durable connection are also contemplated, including, the use of adhesives.

The first and second safety wires 118 and 120 are positioned on opposite sides 132 and 134, respectively, of a distal tip 136 of the mandrel 108 and have contact surfaces 138 and 140, respectively, facing the distal tip 136 of the mandrel 108. The contact surfaces 138 and 140, which may contact the distal tip 136 of the mandrel 108, have a shape other than convex. Contemplated shapes, which will be discussed later in greater detail, may be provided only at contact surfaces 138 and 140, or may extend any length of the first and second safety wires 118 and 120. As such, each of the first and second safety wires 118 and 120 may have a uniform or a non-uniform cross section throughout its length.

Preferably, the proximal end 114 of the mandrel 108 and the proximal end 104 of the helically wound coil 102 are joined together at a second weldment 142, or other similar connection. However, it should be appreciated that the proximal end 114 of the mandrel 108 may be attached to the helically wound coil 102 at another position along the length of the coil 102 or, alternatively, may not be permanently attached to the helically wound coil 102. It should also be appreciated that the proximal ends 122 and 124 of the first and second safety wires 118 and 120 may attach to one or both of the mandrel 108 and the helically wound coil 102 at the second weldment 142.

Figure 2:
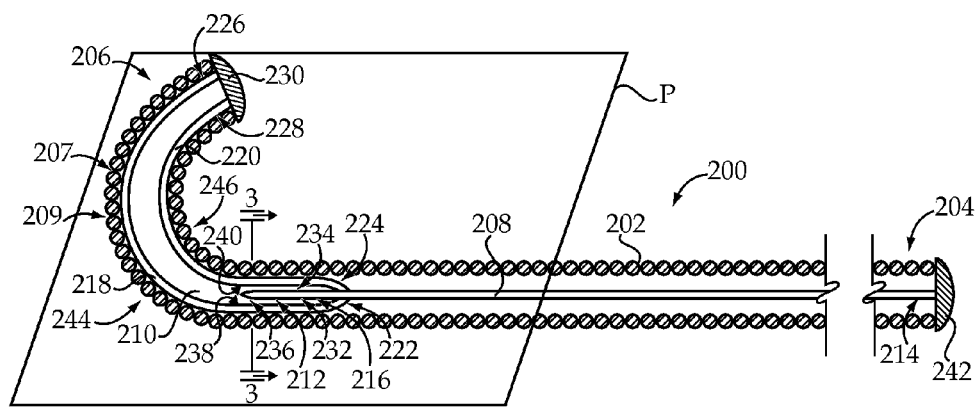
FIG. 2 is a sectional view of a wire guide according to another embodiment of the present disclosure.

Turning now to FIG. 2, another embodiment of a wire guide according to the present disclosure is shown generally at 200. Wire guide 200 is similar to wire guide 100 of FIG. 1 and also includes a helically wound coil 202 having a proximal end 204 and a distal end 206. However, as shown in FIG. 2, a distal segment 207 of the helically wound coil 202 may be curved. As should be appreciated, a variety of preformed shapes may be provided to increase maneuverability of the wire guide 200 into branches of vessels or arteries within a patient.

A mandrel 208, which may be similar to mandrel 108 of FIG. 1, is positioned within the helically wound coil 202 and terminates before the curved distal segment 207, also referred to as a preformed curve 209, of the helically wound coil 202. The mandrel 208 is received within a lumen 210 of the helically wound coil 202 and may include a distal segment 212 that is tapered, starting at any position along the mandrel 208 from a proximal end 214 of the mandrel 108 to a distal end 216 of the mandrel 208.

First and second safety wires 218 and 220 are positioned within the helically wound coil 202 and have proximal ends 222 and 224, respectively, attached to the mandrel 208 and distal ends 226 and 228, respectively, attached to the distal end 206 of the helically wound coil 202. According to the embodiment of FIG. 2, the proximal ends 222 and 224 of the first and second safety wires 218 and 220 may be attached to the mandrel 208 at a location that is closer to the distal end 216 than the proximal end 214. The distal ends 226 and 228 of the first and second safety wires 218 and 220 are preferably attached to the distal end 206 of the helically wound coil 202 at a first weldment 230.

In a manner similar to that described with respect to the embodiment of FIG. 1, the first and second safety wires 218 and 220 are positioned on opposite sides 232 and 234 of a distal tip 236 of the mandrel 208, and have contact surfaces 238 and 240 facing the distal tip 236 of the mandrel 208 that have a shape other than convex. Such shapes and the resulting cross sections of first and second safety wires 218 and 220 will be discussed below with reference to FIGS. 3-5.

The proximal end 214 of the mandrel 208 and the proximal end 204 of the helically wound coil 202 may be joined together at a second weldment 242. Although specific embodiments have been shown, it should be appreciated that numerous modifications or deviations from what is described herein are contemplated. For example, specific materials, shapes, sizes, and attachment means and locations may all vary based on specific use requirements and/or manufacturing constraints.

According to the embodiment of FIG. 2, the first and second safety wires 218 and 220 and preformed curve 209 all occupy a common plane P. Specifically, the first safety wire 218 may occupy an outer curve 244 of the preformed curve 209, while the second safety wire 220 may occupy an inner curve 246 of the preformed curve 209. However, alternative orientations are contemplated.

As stated above, the contact surfaces 138 and 140 of FIG. 1 and contact surfaces 238 and 240 of FIG. 2 have shapes other than convex. For ease of explanation, exemplary shapes will be described with reference to the contact surfaces 238 and 240 of FIG. 2. However, it should be appreciated that similar shapes may be used for contact surfaces 138 and 140 of FIG. 1.

Figure 3:
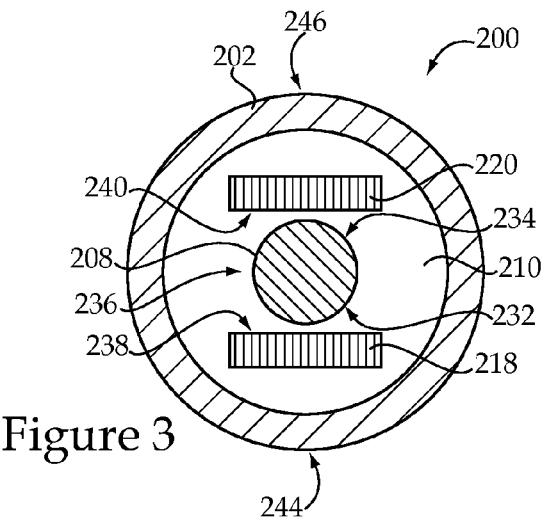
FIG. 3 is a cross sectional view of the wire guide of FIG. 2 taken along lines 3-3 according to one embodiment of the present disclosure.

Turning now to FIG. 3, the contact surfaces 238 and 240 may be substantially flat. Specifically, surfaces of the first and second safety wires 218 and 220 may be substantially flat at portions of the safety wires 218 and 220 that face the mandrel tip 236 or, alternatively, may be substantially flat along all or a majority of lengths of the safety wires 218 and 220 facing the mandrel 208. The first and second safety wires 218 and 220 may contact one or both of the helically wound coil 202 and the mandrel 208 when the wire guide 200 is in use or when the wire guide 200 is not in use. As should be appreciated, safety wires having substantially square or rectangular cross sections may provide a lower profile than safety wires having other cross sections, such as round cross sections, and, thus, may occupy less space within the already limited spatial constraints of the helically wound coil 202. Further, a portion of the additional space may be utilized by extending the width of the safety wires 218 and 220 relative to the mandrel 208, such that additional contact surface area is provided for the mandrel 208 to engage.

Figure 4:
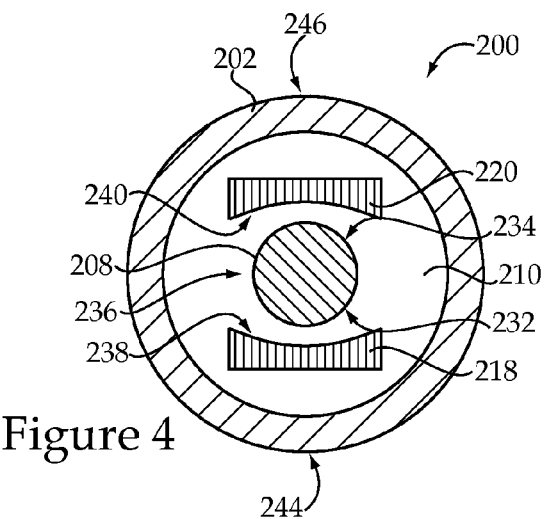
FIG. 4 is a cross sectional view of the wire guide of FIG. 2 taken along lines 3-3 according to another embodiment of the present disclosure.
Figure 5:
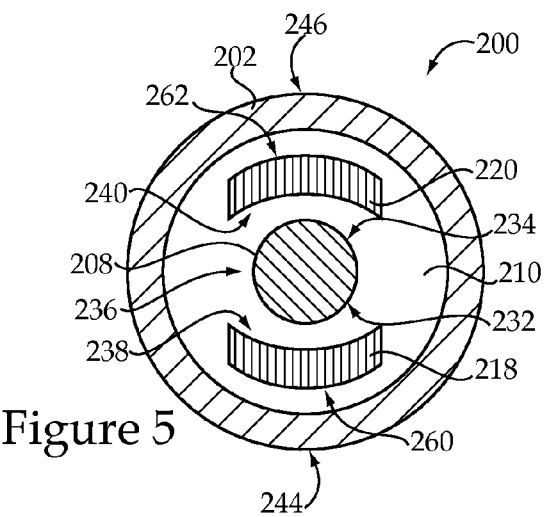
FIG. 5 is a cross sectional view of the wire guide of FIG. 2 taken along lines 3-3 according to yet another embodiment of the present disclosure.

Turning now to FIG. 4, the contact surfaces 238 and 240 are shown as being substantially concave. By utilizing a shape that is complementary to the round cross section of the mandrel 208, the mandrel 208 may be urged and, thereafter, maintained within the concave contact surfaces 238 and 240 during movement, such as bending, of the wire guide 200. Various other shapes, excluding a convex shape, are contemplated for contact surfaces 238 and 240. However, it should be appreciated that sides opposite the contact surfaces 238 and 240 or, more specifically, sides 260 and 262 of the first and second safety wires 218 and 220, as shown in FIG. 5, may include a substantially convex shape. Such shapes at the opposite sides 260 and 262 of respective contact surfaces 238 and 240 may be useful to maintain first and second safety wires 218 and 220 within the outer curve 244 and inner curve 246, respectively. Preferably, and as shown, a width of each of the first and second safety wires 218 and 220 is greater than a width of the distal tip 236 of the mandrel 208.

An exemplary method of making such a wire guide according to the present disclosure will now be described. For ease of explanation, the exemplary method will be described with reference to FIG. 2. However, it should be appreciated that a similar method may be used to make the wire guide 100 of FIG. 1.

According to a first step, the proximal ends 222 and 224 of the first and second safety wires 218 and 220 may be attached to opposite sides 232 and 234 of the mandrel 208 such that substantially flat or substantially concave contact surfaces 238 and 240 of the first and second safety wires 218 and 220, as depicted in FIGS. 3-5, face a distal tip 236 of the mandrel 208. This attachment step may, for example, include soldering the proximal ends 222 and 224 of the first and second safety wires 218 and 220 to the mandrel 208.

The mandrel 208 and the first and second safety wires 218 and 220 may then be inserted into the helically wound coil 202 through the proximal end 204 of the helically wound coil 202 such that the mandrel 208 terminates before the distal end 206 of the helically wound coil 202. Specifically, this step may include inserting the mandrel 208 and the first and second safety wires 218 and 220 into the helically wound coil 202 such that the mandrel 208 terminates before the distal segment 207, particularly if the distal segment 207 is to be shaped into a preformed curve 209.

The distal ends 226 and 228 of the first and second safety wires 218 and 220 may then be welded to the distal end 206 of the helically wound coil 202, such as by using a well known plasma welding technique. In addition, the proximal end 214 of the mandrel 208 may be welded to the proximal end 204 of the helically wound coil 202.

A final step may include shaping the distal segment 207 of the helically wound coil 202 into the preformed curve 209. Alternatively, however, the shaping step may be an initial step of the method. If so, it should be appreciated that the mandrel 208 and the first and second safety wires 218 and 220 may be oriented within the helically wound coil 202 such that the first and second safety wires 218 and 220 and the preformed curve 209 occupy a common plane, such as plane P. This step may preferably be performed prior to the welding steps described above. Shaping wire guides is well known in the art and, therefore, will not be described in detail herein.

Although specific embodiments have been provided, it should be appreciated that various modifications or deviations are contemplated herein. For example, although FIG. 1 illustrates a wire guide 100 that is single-ended (i.e., includes a mandrel 108 terminating before a distal end 106 of a helically wound coil 102 and includes first and second safety wires 118 and 120 having contact surfaces 138 and 140 that flank a distal tip 136 of the mandrel 108), a double-ended construction is also contemplated. In particular, a construction that is similar to the one just described with respect to one end of the wire guide 100 may be provided at both ends of the wire guide 100 such that a proximal end 114 of the mandrel 108 is also tapered and terminates before a proximal end 104 of the helically wound coil 102. Additional safety wires may be provided that include contact surfaces flanking the tapered proximal end 114 of the mandrel 108. In such a configuration, the mandrel 108 may only be attached to the helically wound coil 102 via the safety wires. Further, the double-ended construction may include preformed curves, such as the preformed curve 209 of the embodiment of FIG. 2, formed at each end of the wire guide.

INDUSTRIAL APPLICABILITY

The present disclosure is generally applicable to wire guides for use in percutaneous endovascular procedures. More specifically, the present disclosure is applicable to wire guides having a mandrel positioned within a helically wound coil and terminating before a distal end of the helically wound coil. Further, the present disclosure finds application in procedures during which it is desirable to reduce mandrel protrusions.

Referring generally to FIGS. 1-5 and, more specifically, to the embodiment of FIG. 2, a wire guide 200 may include a helically wound coil 202 having a preformed curve 209. A mandrel 208 is positioned within the helically wound coil 202 and terminates before the preformed curve 209. First and second safety wires 218 and 220 are positioned within the helically wound coil 202 and have proximal ends 222 and 224 attached to the mandrel 208 and distal ends 226 and 228 attached to the distal end 206 of the helically wound coil 202, such as at a first weldment 230. The first and second safety wires 218 and 220 are positioned on opposite sides 232 and 234 of a distal tip 236 of the mandrel 208, and have contact surfaces 238 and 240 facing the distal tip 236 of the mandrel 208 that have a shape other than convex. Specifically, for example, the shapes may be substantially flat, as shown in FIG. 3, or substantially concave, as shown in FIGS. 4 and 5.

The first and second safety wires 218 and 220, having the relative shapes and positioning described herein, are provided to reduce mandrel protrusion during endovascular procedures. Specifically, while advancing the wire guide 200 through blood vessels or arteries of a patient or, more particularly, while the distal end 206 of the helically wound coil 202 is manipulating sharp curves, the distal tip 236 of the mandrel 208 will tend to contact the contact surfaces 238 and 240 rather than strike through the helically wound coil 202. Further by utilizing two safety wires 218 and 220 that are both welded to the distal end 206 of the helically wound coil 202 at distal ends 226 and 228 thereof, testing has indicated that the tensile strength of the weld joint, or first weldment 230, is significantly increased. These benefits, as should be appreciated, will also be recognized in embodiments that do not include the preformed curve 209.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A method of making a wire guide, wherein the wire guide includes a mandrel positioned within a helically wound coil, and first and second safety wires positioned within the helically wound coil and having proximal ends attached to the mandrel and distal ends attached to a distal end of the helically wound coil, the method comprising the steps of:

attaching the proximal ends of the first and second safety wires to opposite sides of the mandrel such that substantially flat contact surfaces or substantially concave contact surfaces of the first and second safety wires face a distal tip of the mandrel;

inserting the mandrel and the first and second safety wires into the helically wound coil through a proximal end of the helically wound coil such that the mandrel terminates before the distal end of the helically wound coil; and welding the distal ends of the first and second safety wires to the distal end of the helically wound coil.

2. The method of claim 1, wherein the attaching step includes soldering the proximal ends of the first and second safety wires to the mandrel.

3. The method of claim 2, further including shaping a distal segment of the helically wound coil into a preformed curve.

4. The method of claim 3, wherein the inserting step includes inserting the mandrel and the first and second safety wires into the helically wound coil such that the mandrel terminates before the preformed curve.

5. The method of claim 4, further including orienting the mandrel and the first and second safety wires within the helically wound coil such that the first and second safety wires and the preformed curve occupy a common plane, wherein the orienting step is performed prior to the welding step.

6. The method of claim 5, further including welding a proximal end of the mandrel to the proximal end of the helically wound coil.

* * * * *